United States Patent
Turnbow et al.

(10) Patent No.: US 10,575,916 B2
(45) Date of Patent: Mar. 3, 2020

(54) SURFACTANT TREATMENT FOR A STERILIZATION WRAP WITH REDUCED OCCURRENCE OF WET PACKS AFTER STEAM STERILIZATION

(71) Applicant: O&M Halyard, Inc., Mechanicsville, VA (US)

(72) Inventors: Catherine J. Turnbow, Alpharetta, GA (US); Roger B. Quincy, III, Alpharetta, GA (US); Anthony Stephen Spencer, Alpharetta, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 262 days.

(21) Appl. No.: 15/127,065

(22) PCT Filed: Feb. 27, 2015

(86) PCT No.: PCT/US2015/018028
§ 371 (c)(1),
(2) Date: Sep. 19, 2016

(87) PCT Pub. No.: WO2015/131054
PCT Pub. Date: Sep. 3, 2015

(65) Prior Publication Data
US 2017/0172682 A1 Jun. 22, 2017

Related U.S. Application Data

(63) Continuation of application No. 14/193,374, filed on Feb. 28, 2014, now abandoned.

(51) Int. Cl.
*A61B 50/33* (2016.01)
*D06M 13/00* (2006.01)
(Continued)

(52) U.S. Cl.
CPC ........... *A61B 50/33* (2016.02); *A61L 2/07* (2013.01); *D06M 13/10* (2013.01); *D06M 13/17* (2013.01);
(Continued)

(58) Field of Classification Search
CPC .. D06M 13/17; D06M 13/248; D06M 13/292; D06M 13/513; D06M 15/53;
(Continued)

(56) References Cited

U.S. PATENT DOCUMENTS

| | | | |
|---|---|---|---|
| 3,338,992 | A | 8/1967 | Kinney |
| 3,341,394 | A | 9/1967 | Kinney |

(Continued)

FOREIGN PATENT DOCUMENTS

| | | |
|---|---|---|
| CN | 1565701 A | 1/2005 |
| GB | 2 360 707 B | 11/2002 |

(Continued)

OTHER PUBLICATIONS

Abstract of Brazilian Patent—BRPI0702674, Feb. 17, 2009, 2 pages.
(Continued)

*Primary Examiner* — Jeremy R Pierce
(74) *Attorney, Agent, or Firm* — Dority & Manning, P.A.

(57) ABSTRACT

A surfactant treatment is provided that can result in a sterilization wrap that can have a bacterial filtration efficiency of at least 94 percent as determined according to ASTM F2101. The surfactant treatment includes a surfactant consisting essentially of carbon, hydrogen, and oxygen atoms. Wrapping packs in a wrap treated with said surfactant treatment in an amount ranging from greater than 0 to 2 weight percent based on the dry weight of the wrap results in the production of fewer wet packs after steam sterilization compared to when packs are wrapped with an identical wrap
(Continued)

without said surfactant treatment. A sterilization wrap comprising a nonwoven fabric and a dried residue surfactant treatment that is essentially free of silicon, potassium, phosphorus, and sulfur is also provided, where wrapping packs to be sterilized in the surfactant treated wrap reduces the occurrence of wet packs after steam sterilization compared using an untreated wrap.

18 Claims, 2 Drawing Sheets

(51) Int. Cl.
  *A61L 2/07* (2006.01)
  *D06M 15/53* (2006.01)
  *D06M 13/17* (2006.01)
  *D06M 13/248* (2006.01)
  *D06M 13/292* (2006.01)
  *D06M 13/513* (2006.01)
  *D06M 13/10* (2006.01)
  *A61B 50/30* (2016.01)
  *A61B 46/00* (2016.01)
  *D06M 101/20* (2006.01)
  *D06M 101/18* (2006.01)

(52) U.S. Cl.
  CPC ........ *D06M 13/248* (2013.01); *D06M 13/292* (2013.01); *D06M 13/513* (2013.01); *D06M 15/53* (2013.01); *A61B 46/00* (2016.02); *A61B 50/30* (2016.02); *A61L 2202/24* (2013.01); *D06M 2101/18* (2013.01); *D06M 2101/20* (2013.01); *D06M 2200/12* (2013.01); *Y10T 442/20* (2015.04)

(58) Field of Classification Search
  CPC .. D06M 2101/20; A61L 2/07; A61L 2202/24; A61B 46/00; A61B 50/30; Y10T 442/20
  See application file for complete search history.

(56) References Cited

U.S. PATENT DOCUMENTS

| | | | |
|---|---|---|---|
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,340,563 A | 7/1982 | Appel et al. | |
| 5,057,368 A | 10/1991 | Largman et al. | |
| 5,069,970 A | 12/1991 | Largman et al. | |
| 5,151,321 A * | 9/1992 | Reeves ................... | A61L 31/10 442/400 |
| 5,277,976 A | 1/1994 | Hogle et al. | |
| 5,308,691 A | 5/1994 | Lim et al. | |
| 5,466,410 A | 11/1995 | Hills | |
| 5,484,645 A | 1/1996 | Lickfield et al. | |
| 5,592,357 A | 1/1997 | Rader et al. | |
| 5,616,408 A | 4/1997 | Oleszczuk et al. | |
| 5,635,134 A * | 6/1997 | Bourne ..................... | A61L 2/07 422/26 |
| 5,804,512 A | 9/1998 | Lickfield et al. | |
| 5,834,386 A | 11/1998 | Cohen | |
| 5,879,620 A | 3/1999 | Cohen | |
| 5,981,038 A | 11/1999 | Weimer et al. | |
| 6,063,498 A | 5/2000 | Licht et al. | |
| 6,204,208 B1 * | 3/2001 | Krzysik ............... | A61F 13/8405 442/400 |
| 6,406,764 B2 | 6/2002 | Bayer | |
| 6,780,226 B1 | 8/2004 | Lifshutz et al. | |
| 6,858,551 B1 | 2/2005 | Turkevich et al. | |
| 7,018,945 B2 | 3/2006 | Yahiaoui et al. | |
| 7,022,630 B2 | 4/2006 | Berman et al. | |
| 7,378,451 B2 | 5/2008 | Levitt et al. | |
| 7,560,082 B2 | 7/2009 | Stecklein et al. | |
| 7,879,746 B2 | 2/2011 | Klun et al. | |
| 8,261,963 B2 | 9/2012 | Gaynor et al. | |
| 8,323,554 B2 | 12/2012 | Leonard | |
| 8,721,943 B2 | 5/2014 | Moore et al. | |
| 8,783,003 B2 | 7/2014 | Czajka, Jr. et al. | |
| 9,062,914 B2 | 6/2015 | Sweeney | |
| 9,194,065 B2 | 11/2015 | Moore et al. | |
| 2002/0106959 A1 | 8/2002 | Huffines et al. | |
| 2004/0000313 A1 | 1/2004 | Gaynor et al. | |
| 2005/0079379 A1 | 4/2005 | Wadsworth et al. | |
| 2005/0268817 A1 | 12/2005 | Iwata et al. | |
| 2006/0067855 A1 | 3/2006 | Mathis et al. | |
| 2010/0028575 A1 | 2/2010 | Vanhamel | |
| 2011/0117176 A1 | 5/2011 | Klun et al. | |
| 2013/0111852 A1 | 5/2013 | Farmer et al. | |
| 2015/0247281 A1 | 9/2015 | Turnbow et al. | |

FOREIGN PATENT DOCUMENTS

| | | |
|---|---|---|
| JP | H 0472166 A | 3/1992 |
| WO | WO 99/32706 A1 | 7/1999 |
| WO | WO 00/00267 A2 | 1/2000 |
| WO | WO 00/00267 A3 | 1/2000 |
| WO | WO 00/12801 A1 | 3/2000 |
| WO | WO 2008/083426 A1 | 7/2008 |
| WO | WO 2009/143551 A1 | 12/2009 |

OTHER PUBLICATIONS

Abstract of Brazilian Patent—BRPI0804047, Jun. 29, 2010, 2 pages.
Abstract of EP Patent—EP0137094, Jul. 1, 1987, 1 page.
Abstract of EP Patent—EP1997516, Dec. 3, 2008, 1 page.
Abstract of Japanese Patent—JPH0892859, Apr. 9, 1996, 2 pages.
International Search Report and Written Opinion for PCT/US2015/018028 dated Jun. 2, 2015, 12 pages.

* cited by examiner

SURFACTANT TREATMENT FOR A STERILIZATION WRAP WITH REDUCED OCCURRENCE OF WET PACKS AFTER STEAM STERILIZATION

RELATED APPLICATIONS

This application is the national stage entry of International Patent Application No, PCT/US2015/018028 having a filing date of Feb. 27, 2015, which claims priority to U.S. patent application Ser. No. 14/193,374, filed on Feb. 28, 2014, now abandoned, both of which are incorporated herein in their entirety by reference thereto.

BACKGROUND

This disclosure relates to reducing the incidence of water remaining on steam sterilized packages in a medical setting.

Items used in medical settings such as gowns, sheets, drapes, and instruments used during surgery or other aseptic procedures are used on a daily basis. If these items are not received from a manufacturer in a sterile state, it is necessary for the medical facility to sterilize them before use. If these items are not disposable and are used more than once, it is required that they be sterilized prior to reuse. To sterilize medical items, they are normally first packaged within a protective sheet material wrap and then subject to the steam sterilization procedure. Occasionally, packages emerge from the sterilization process with moisture visible on the wrap. If this occurs, the tray must be rejected.

It is also important to maintain the sterility of the items inside the sterilized, wrapped package until the package is opened. Therefore, a wrap must be able to resist the penetration of bacteria, and must act as a filter to particles that can carry bacteria. Bacterial filtration efficiency (BFE) is a measure of how easily bacteria can pass through the sheet material used to wrap the medical items. A higher BFE indicates that the wrapped, sterilized items should remain bacteria free for a longer period of time than similar sterilized items wrapped with a lower BFE wrap material.

Appropriate protective sheet material includes those as shown, for example, in U.S. Pat. No. 5,635,134 to Bourne, et al., which discloses a multi-ply sterilization wrap that is formed by joining one or more sheets of sterilization wrap (e.g., two separate sheets or one sheet folded over) together to form two similarly sized, superposed panels that allow convenient dual wrapping of an article. As another example, U.S. Patent Publication No. 2001/0036519 by Robert T. Bayer discloses a two ply sterilization wrap that is formed of a single sheet of sterilization wrap material that is folded to form two similarly sized, superposed panels that are bonded to each other. As yet another example, U.S. Patent Publication No. 2005/0163654 by Stecklein, et al. discloses a sterilization wrap material that has a first main panel and a second panel that is smaller than the main panel. The second panel is superposed and bonded to the central portion of the main panel such that it is contained entirely within the main panel to reinforce the main panel and/or provide additional absorbency. U.S. Pat. No. 8,261,963 to Gaynor, et al. discloses a multi-panel sterilization assembly that includes a barrier panel composed of a permeable sheet material having barrier properties, panel attachment means for securing the barrier panel into a package; and a fold protection panel. The barrier panel includes: a first surface and a second opposing surface; a first end generally defining a pre-determined fold line; a second end opposite the first end; a first edge that is generally perpendicular to the pre-determined fold line; a second edge that is generally opposite the pre-determined fold line; and a third edge that is generally perpendicular to the pre-determined fold line. Sterilization wraps may also have a single ply only and these are suitable for use with this disclosure.

Sterilization wraps are commonly made from non-woven materials made by the spunbonding and meltblowing processes and are often electret treated to increase the bacterial filtration efficiency. Electret treatment is described, for example, in U.S. Pat. No. 5,592,357 to Rader, et al.

Items subjected to steam sterilization can sometimes emerge from the sterilization process still containing visible water. These water-containing steam sterilized packages are referred to as "wet packs" and require re-sterilization, costing the medical facility time and money. Reduction in wet packs while maintaining an acceptable BFE level is highly desirable.

SUMMARY

The present disclosure describes a surfactant treatment including a surfactant that consists essentially of carbon, hydrogen, and oxygen atoms. A polyolefinic nonwoven fabric sterilization wrap treated with said surfactant treatment in an amount ranging from greater than 0 weight percent to 2 weight percent based on the dry weight of said polyolefinic nonwoven fabric sterilization wrap results in the production of fewer wet packs after steam sterilization when the packs are wrapped with said surfactant treated polyolefinic nonwoven fabric sterilization wrap as compared to when the packs are wrapped with an identical polyolefinic nonwoven fabric sterilization wrap without said surfactant treatment. In some embodiments, the resulting surfactant treated polyolefinic nonwoven fabric sterilization wrap can have a BFE after sterilization of at least 94 percent and if, electret treated, the surfactant treated polyolefinic nonwoven fabric sterilization wrap can have a BFE after steam sterilization of at least 97 percent.

The present disclosure also describes a sterilization wrap comprising a polyolefinic nonwoven fabric and a dried residue of an aqueously applied surfactant treatment. The surfactant treatment includes a surfactant, wherein said surfactant is essentially free of silicon, potassium, phosphorus, and sulfur. Further, the dried residue of the aqueously applied surfactant treatment is present in an amount ranging from greater than 0 weight percent to 2 weight percent based on the dry weight of the polyolefinic nonwoven fabric. The surfactant treatment results in the production of fewer wet packs after steam sterilization when the packs are wrapped with said surfactant treated polyolefinic nonwoven fabric sterilization wrap as compared to when the packs are wrapped with an identical polyolefinic nonwoven fabric sterilization wrap without said surfactant treatment. In some embodiments, the sterilization wrap can have a BFE after sterilization of at least 94 percent and if, electret treated, the surfactant treated sterilization wrap can have a BFE after steam sterilization of at least 97 percent.

A method of reducing the occurrence of wet packs post sterilization is also described in the present disclosure. The method includes the steps of providing a nonwoven fabric sterilization wrap; applying a surfactant treatment including a surfactant, wherein said surfactant consists essentially of carbon, hydrogen and oxygen atoms, to said nonwoven fabric, in an amount ranging from greater than 0 weight percent to 2 weight percent based on the dry weight of the nonwoven fabric sterilization wrap; drying said surfactant treated nonwoven fabric sterilization wrap; wrapping items to be sterilized in said surfactant treated nonwoven fabric sterilization wrap; and steam sterilizing the wrapped items. Further, sterilizing the wrapped items with the surfactant treated nonwoven fabric sterilization wrap results in the production of fewer wet packs after steam sterilization as compared to when the items are wrapped with an identical nonwoven fabric sterilization wrap without said surfactant treatment.

In an additional embodiment, the present disclosure contemplates a surfactant treatment including a surfactant, said surfactant consisting essentially of carbon, hydrogen, and oxygen atoms, wherein a polyolefinic nonwoven fabric sterile wrap treated with said surfactant treatment exhibits a bacterial filtration efficiency after electret treatment and after steam sterilization of at least 97 percent as determined according to ASTM F2101.

In yet another embodiment, the present disclosure contemplates a sterilization wrap comprising a nonwoven fabric and a dried residue of an aqueously applied surfactant treatment, wherein said surfactant treatment includes a surfactant, wherein said surfactant is essentially free of silicon, potassium, phosphorus, and sulfur, wherein said sterilization wrap has a bacterial filtration efficiency after electret treatment and after steam sterilization of at least 97 percent as determined according to ASTM F2101.

BRIEF DESCRIPTION OF THE FIGURES

A full and enabling disclosure of the present disclosure, including the best mode thereof to one skilled in the art, is set forth more particularly in the remainder of the specification, including reference to the accompany figures, in which.

Figure 1:
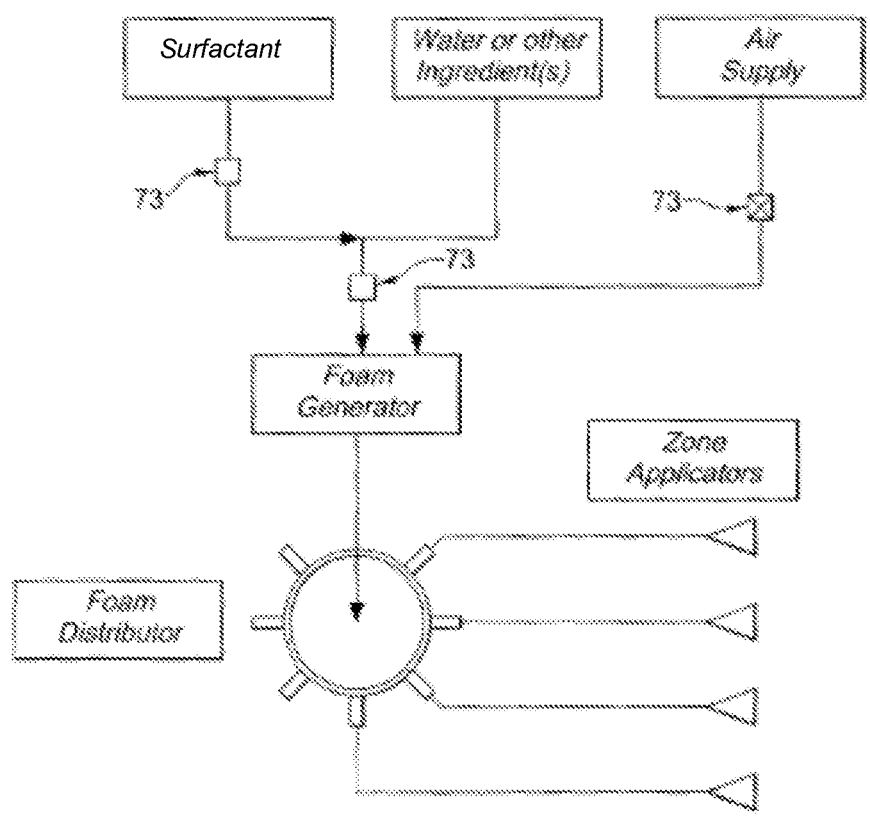
FIG. 1 schematically illustrates a foam surfactant treatment application system that can be used in forming the nonwoven fabric sterilization wrap of the present disclosure.

Repeat use of reference characters in the present specification and drawings is intended to represent the same or analogous features or elements of the present disclosure.

DETAILED DESCRIPTION

It is to be understood that the following description is only exemplary of the principles of the present disclosure and should not be viewed as narrowing the pending claims. Those skilled in the art will appreciate that aspects of the various embodiments discussed may be interchanged and modified without departing from the scope and spirit of the disclosure.

Items such as medical trays containing surgical instruments are wrapped, generally with a nonwoven fabric wrap, and steam sterilized. If, after sterilization, any visible moisture is observed on the wrap or inside the tray, the tray must be rejected. Sterilized trays should be wrapped in materials having high bacterial filtration efficiency (BFE) so that they remain bacteria free until they are opened for use.

One exemplary sterilization wrap for use in the present disclosure is a spunbond/meltblown/spunbond (SMS) material like that described in U.S. Pat. No. 8,261,963. The basis weight of such SMS material(s) may be from 1 ounce per square yard or "osy" (which is approximately 33 grams per square meter or "gsm") to about 3 osy (100 gsm). For example, the basis weight of the SMS material(s) may be from 1.2 osy (40 gsm) to about 2 osy (68 gsm). As another example, the basis weight of the SMS material(s) may be from 1.4 osy (47 gsm) to about 2.6 osy (88 gsm). The basis weight may be determined in accordance with ASTM D3776-07. Multiple plies or layers of SMS material may be used to provide basis weights ranging from about 2 osy (67 gsm) to about 6.1 osy (200 gsm).

As used herein, the term "nonwoven fabric or web" means a web having a structure of individual fibers or threads which are interlaid, but not in an identifiable manner as in a knitted fabric. Nonwoven fabrics or webs have been formed from many processes such as, for example, meltblowing processes, spunbonding processes, and bonded carded web processes. The basis weight of nonwoven fabrics is usually expressed in ounces of material per square yard (osy) or grams per square meter (gsm), and the fiber diameters useful are usually expressed in microns. (Note that to convert from osy to gsm, multiply osy by 33.91).

As used herein, the term "spunbonded fibers" refers to small diameter fibers that are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel, et al., and U.S. Pat. No. 3,692,618 to Dorschner, et al., U.S. Pat. No. 3,802,817 to Matsuki, et al., U.S. Pat. Nos. 3,338,992 and 3,341,394 to Kinney, U.S. Pat. No. 3,502,763 to Hartman, and U.S. Pat. No. 3,542,615 to Dobo, et al. Spunbond fibers are generally not tacky when they are deposited onto a collecting sheet. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle, et al., U.S. Pat. No. 5,466,410 to Hills, and U.S. Pat. Nos. 5,069,970 and 5,057,368 to Largman, et al., which describe fibers with unconventional shapes.

As used herein, the term "meltblown fibers" means fibers formed by extruding a molten thermoplastic material through a plurality of fine, usually circular, die capillaries as molten threads or filaments into converging high velocity, usually hot, gas (e.g., air) streams, which attenuate the filaments of molten thermoplastic material to reduce their diameter, which may be to microfiber diameter. Thereafter, the meltblown fibers are carried by the high velocity gas stream and are deposited on a collecting sheet to form a web of randomly dispersed meltblown fibers. Such a process is disclosed, for example, in U.S. Pat. No. 3,849,241 to Butin, et al. Meltblown fibers are microfibers that may be continuous or discontinuous, are generally smaller than 10 microns in average diameter, and are generally tacky when deposited onto a collecting sheet.

The permeability of the wrap material may range from 25 to about 500 cubic feet per minute (CFM) as characterized in terms of Frazier permeability. For example, the permeability of the wrap material may range from 50 to about 400 cubic feet per minute. As yet another example, the permeability of the wrap material may range from 100 to about 300 cubic feet per minute. The Frazier permeability, which expresses the permeability of a material in terms of cubic feet per minute of air through a square foot of area of a surface of the material at a pressure drop of 0.5 inch of water (or 125 Pa), was determined utilizing a Frazier Air Permeability Tester available from the Frazier Precision Instrument Company and measured in accordance with Federal Test Method 5450, Standard No. 191A. When the wrap material contains SMS material(s) having basis weights ranging from about 1 osy (33 gsm) to about 2.6 osy (88 gsm), the permeability of the wrap material may range from about 20 cubic feet per minute to about 75 cubic feet per minute when determined generally in accordance with ISO 9237:1995 (measured with an automated air permeability machine using a 38 cm$^2$ head at a test pressure of 125 Pa—an exemplary air permeability machine is TEXTEST FX 3300 available from TEXTEST AG, Switzerland). If multiple plies or layers of SMS material are used to provide basis weights ranging from about 2 osy (67 gsm) to about 5.2 osy (176 gsm), the permeability of the wrap material may range from about 10 cubic feet per minute to about 30 cubic feet per minute when determined generally in accordance with ISO 9237:1995.

There are a number of methods of characterizing the air filtration efficiencies of nonwoven webs. One method uses a TSI, Inc. (St. Paul, Minn.) Model 8130 Automated Filter Tester (AFT). This test (the TSI test) is less expensive than the BFE test, and while less accurate, gives directional and relative indications of filtration efficiency. The Model 8110 AFT measures pressure drop and particle filtration characteristics for air filtration media. The AFT utilizes a compressed air nebulizer to generate a sub-micron aerosol of sodium chloride particles that serves as the challenge aerosol for measuring filter performance. The characteristic size of the particles used in these measurements was 0.1 micrometer. Typical air flow rates were between 31 liter per minute and 85 liters per minute. The AFT test was performed on a sample area of 140 square cm. The performance or efficiency of a filter medium is expressed as the percentage of sodium chloride particles that penetrate the filter.

Penetration is defined as transmission of a particle through the filter medium. The transmitted particles were detected downstream from the filter. The percent penetration (% P) reflects the ratio of the downstream particle count to the upstream particle count. Light scattering was used for the detection and counting of the sodium chloride particles.

Bacterial filtration efficiency (BFE) employs a test where samples are challenged with a biological aerosol of Staphylococcus aureus (S. aureus) and the results employ a ratio of the bacterial challenge counts to sample effluent counts to determine percent bacterial filtration efficiency (% BFE). For the tests herein, a suspension of S. aureus was aerosolized using a nebulizer and delivered to the test article at a constant flow rate. The aerosol droplets were drawn through a six-stage, viable particle Andersen sampler for collection. This test procedure allows a reproducible bacterial challenge to be delivered to the sterilization wrap and complies with ATSM F2101 (Nelson Lab #373162). The testing herein was performed by Nelson Laboratories, Inc., Salt Lake City, Utah, according to "Bacterial Filtration Efficiency," Procedure No. SOP/ARO/007L.1. The acceptable BFE for a sterilization wrap is desirably at least 94 percent, more desirably 97 percent, and still more desirably 98 percent or greater (e.g., 99 percent or 99.7 percent). For example, a multiple-ply sterilization wrap such as one described by, for example, U.S. Pat. No. 5,635,134 or U.S. Patent Application Publication No. 2013/0111852 A1, will desirably have BFE of at least 97 percent more desirably 98 percent, and still more desirably 99 percent or greater, As another example, a single ply sterilization wrap having BFE of less than 97 percent may be used according to a current practice for such single ply sterilization wraps by wrapping an article to be sterilized with a first single ply sterilization wrap and then wrapping it with a second single ply sterilization wrap in sequence to create a package containing multiple plies of sterilization wrap that collectively have BFE of at least 97 percent, more desirably 98 percent, and still more desirably 99 percent or greater. Of course, it is contemplated that a sterilization wrap (either multiple-ply or single ply) may have BFE that is less than 97 percent (e.g., 94 percent, 95 percent or 96 percent) while still providing useful service as a sterilization wrap in certain, limited circumstances.

The Andersen sampler is known in the art and is used to collect viable samples of airborne bacteria and fungal spores. The samples can act as a measure of the number of bacteria or fungal spores in the air at a specific location and time. The sampler works through impaction in which air is drawn through a sampling head with 400 small holes at constant rate (in this case 28.3 L/min or 1 cubic foot per minute) for a known period of time. Before sampling, a media plate is placed inside the sampling head, and as air is pulled through the holes, heavier particles such as, e.g., bacteria and fungal spores impact on the agar surface and stick there. The air continues through the sampler and into the pump. After sampling, the plate can be removed for culturing.

It has been found that electret treatment increases the BFE of a fabric. Electret treatment is described, for example, in U.S. Pat. No. 5,592,357 to Rader, et al. Electret treatment is used to produce an intense corona current at reduced voltages to help reduce the potential for arcing and provide a more efficient, stable discharge at atmospheric pressure, for electrostatically charging an advancing web or film. Once ionization occurs, excess charged particles cannot be lost until they collide with a solid body, preferably the remaining electrode, achieving the desired result. It has been found that this applies to both AC and DC voltages.

Placement of a thin, non-electron absorbing gas layer in the vicinity of an electrode is advantageously accomplished by various means. For example, the charging bar can be replaced with a longitudinally extending tube having spaced apertures for delivering a gas to the discharge-forming elements of the electrode. These discharge-forming elements can include either a series of pins that extend through the spaced apertures of the tube, or a series of nozzles that project from the surface of the tube. In either case, this places the gas in the vicinity of the pins, or the nozzles, which in turn receive appropriate biasing voltages for developing the electric field that is to produce the improved discharge. Alternatively, the charging shell can be replaced with a hollow body that similarly incorporates a series of apertures, and a cooperating series of pins or nozzles, to achieve a similar result.

It is to be understood that the nonwoven fabric sterilization wrap of the present disclosure can be electret treated either before or after a surfactant treatment, where the surfactant treatment can facilitate the spread of moisture produced during steam sterilization across the nonwoven fabric sterilization wrap in an even manner, resulting in the reduction in the number of wet packs produced post-sterilization. It is also to be understood that the electret treatment can be optional in some embodiments. Turning now to application of the surfactant treatment specifically, any suitable method or system can be used to apply the surfactant treatment. For instance, a dip and squeeze method can be used where the nonwoven fabric is dipped in a surfactant solution, or the surfactant treatment can be applied using a foaming treatment process such as the foam treatment process described in U.S. Pat. No. 7,018,945 to Yahiaoui, et al. Foaming can be a desirable process because of its efficiency, ease of operation, cleanliness, and good control over process parameters. A general schematic diagram of a foam process is shown in FIG. 1 and includes chemical tanks, air and water supplies, and metering devices 73 (e.g. pumps, valves and flow meters) connected to a high shear-mixing chamber. Suggested foam equipment can be obtained from Gaston Systems, Incorporated of Stanley, N.C. This equipment includes a parabolic foam applicator with a ⅛ inch slot opening and a slot width that is adjustable from about 11 inches to about 18 inches, but can be as wide as 120 inches or more. This kind of foam equipment is capable of full width treatment or zoned treatment. A zoned treatment can be achieved by using foam applicator of a specific width, e.g. 4 inches wide. In the case of zoned treatment, multiple 4 inch wide foam applicators can be used to simultaneously treat multiple slits of a nonwoven base roll as illustrated in FIG. 2.

Figure 2:
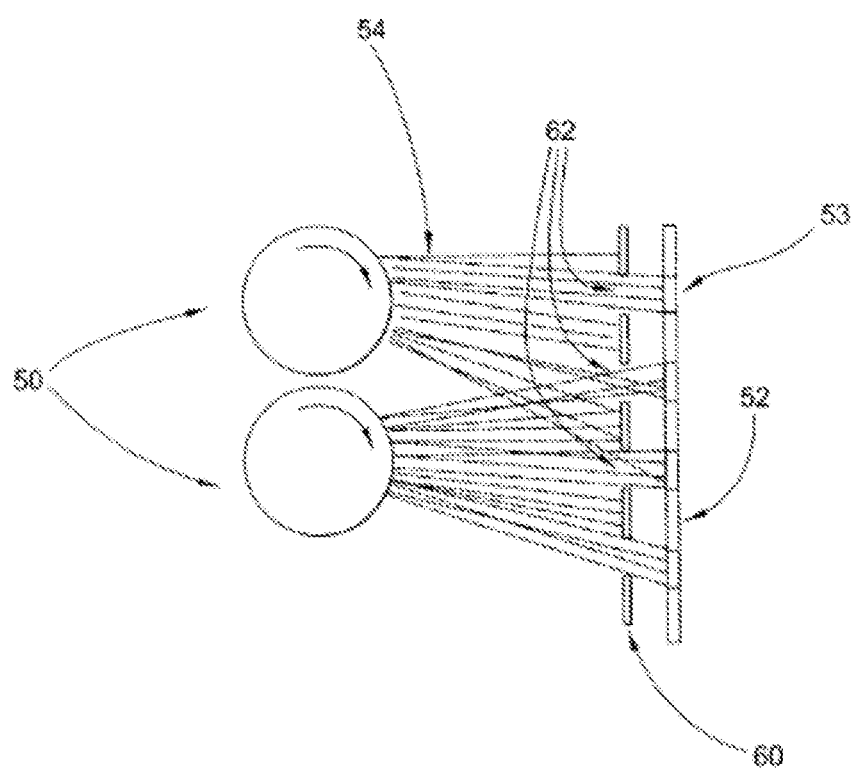
FIG. 2 schematically illustrates an alternative surfactant treatment application system that can be used in forming the nonwoven fabric sterilization wrap of the present disclosure.

FIG. 2 illustrates an exemplary rotary spray zoned treatment application apparatus and system. A suggested system and apparatus that includes the components illustrated in the figures includes a "WEKO" system. The WEKO system and apparatus can be obtained from WEKO, Biel AG, Switzerland. The configuration includes a centrifugal damping application system using a single or double rotocarrier. The surfactant treatment is pumped to the header through a gear pump where it is fed to the damping rotors through restrictor tubes. The system is equipped with a series of rotors 50, which spin can at a speed of about 4500 rpm. Under the effect of a centrifugal force generated by the spinning rotors 50, a surfactant treatment can be dispensed to the nonwoven fabric or other substrate 52 in the form of an aerosol or small droplets 54. Throughput as measured in grams/minute is controlled and adjusted with different diameter restrictor tubes, header pressure and bath parameters (e.g. concentration and temperature). Additionally, finer throughput control can be achieved by adding optional needle valves to the outlet ports of the header. If a zone treatment is desired, templates 60 made of stainless steel or another solid material of a predetermined width are placed in front of the web so that the spray is applied to the nonwoven fabric only through the template opening(s) 62. A suggested template opening is 4 inches and provides a 4-inch wide treated zone 53 to a nonwoven fabric 52.

Various other methods may also be employed for contacting a nonwoven fabric sterilization wrap with the surfactant treatment in accordance with the invention. For example, a nonwoven fabric sterilization wrap may be printed on by means of print rolls, slot coating, or other conventional coating techniques. Regardless of the method by which the surfactant treatment is applied to the sterilization wrap, the surfactant treatment can be applied in an amount ranging from above 0 weight percent to about 2 weight percent, desirably above 0 weight percent to about 1.5 weight percent, more desirably in an amount ranging from about 0.1 weight percent to about 1.5 weight percent, based on the dry weight of said nonwoven fabric sterilization wrap. For example, the surfactant treatment can be applied in an amount ranging from about 0.1 weight percent to about 2 weight percent, desirably in an amount ranging from about 0.1 weight percent to about 1 weight percent, more desirably about 0.2 to about 0.5 weight percent, based on the dry weight of said nonwoven fabric sterilization wrap. More particularly, the amount of surfactant treatment is expressed as a weight percent of the surfactant ingredient (i.e., the weight of surfactant ingredient excluding any carrier such as water) based on the dry weight of the nonwoven fabric sterilization wrap.

Turning now to the sterilization of items or packs (e.g., trays, instruments, tools, devices, or any other item or combination thereof that typically requires sterilization as known in the art) wrapped with the nonwoven fabric sterilization wrap after subjecting the nonwoven fabric sterilization wrap to surfactant and electret treatment, of all the methods available for sterilization, moist heat in the form of saturated steam under pressure is the most widely used and the most dependable. Steam sterilization is nontoxic, inexpensive, rapidly microbicidal, sporicidal, and rapidly heats and penetrates fabrics. The basic principle of steam sterilization, as accomplished in an autoclave, is to expose each item to direct steam contact at the required temperature and pressure for the specified time. Thus, there are four parameters of steam sterilization: steam, pressure, temperature, and time. The ideal steam for sterilization is dry saturated steam and entrained water (dryness fraction ≥97%). Pressure serves as a means to obtain the high temperatures necessary to quickly kill microorganisms. Specific temperatures must be obtained to ensure the microbicidal activity. The two common steam-sterilizing temperatures are 121° C. (250° F.) and 132° C. (270° F.). These temperatures (and other high temperatures) must be maintained for a minimal time to kill microorganisms. Recognized minimum exposure periods for sterilization of wrapped healthcare supplies are 30 minutes at 121° C. (250° F.) in a gravity displacement sterilizer or 4 minutes at 132° C. (270° F.) in a pre-vacuum sterilizer. Additionally, the Creutzfeldt-Jakob Disease (CJD) prion cycle is carried out at 134° C. (273° F.) for 18 minutes in a pre-vacuum sterilizer. Sterilization for the BFE tests herein took place at 134° C. (273° F.) for 3 minutes.

The criteria for deciding that a wet pack exists after sterilization is two-fold; firstly, is the item's (e.g., tray's) weight after (i.e., post) sterilization higher than the pre-sterilization weight by 3 percent or more? Secondly, is there any sign of moisture visible on the top of the item/tray or inside of the item/tray after sterilization? If the answer to either or both of these questions is "yes," then the item/tray is a wet pack.

Surfactant treatments for the nonwoven sterilization wrap were investigated, in the belief that a more wettable wrap would result in fewer wet packs since the moisture would spread out on the wrap, thus covering more surface area and evaporating more easily and quickly. The wrap used in the testing was a 2.57 osy (87 gsm) SMS, except for Sample 1, which was a 1.85 osy (62.7 gsm) SMS. The surfactant treatment for Samples 1-9 was applied to the wrap by a dip and squeeze (saturation) process so that an outwardly-facing surface of the wrap and an inner-facing surface of the wrap were contacted with the surfactant treatment, using an aqueous formulation containing the surfactant, while the surfactant treatment for Samples 11-14 was applied to the outwardly-facing surface of the wrap using the foam treatment process described above. The amount of surfactant treatment in weight percent is indicated in the Sample descriptions below for the treated and dried wrap. For Samples 1-9, the wrap having the dried surfactant treatment residue was subjected to electret treatment as indicated in the Table, while for Samples 11-14, the wrap was electret treated before applying the surfactant treatment. The trays were wrapped using a double layer wrap having an outwardly-facing surface and an inner-facing surface according to the method of U.S. Pat. No. 5,635,134, sterilized at 134° C. (273° F.), and tested for wet packs. TSI and BFE were tested according to the procedures above.

Samples with treatments that were tested include the following:
1. Quadrastat® PIBK at 0.8% add on based on the dry weight of the wrap: Quadrastat® PIBK is the tradename for an aqueous formulation that contains 50% of potassium isobutyl phosphate available from Manufacturers Chemicals, LLCP, of Cleveland, Tenn. The data in the table is based on five samples.
2. Quadrastat® PIBK at 3.0% add on based on the dry weight of the wrap: The data in the table is based on five samples.
3. MASIL® SF 19 at 0.8% add on based on the dry weight of the wrap: MASIL® SF 19 is a low toxicity silicone surfactant with high thermal stability combining the advantages of dimethyl silicone fluids with conventional, nonionic surfactants. This product has a polydimethyl-siloxane backbone modified via the chemical attachment of polyoxyalkylene chains. MASIL® SF 19 provides reduced surface tension in aqueous and non-aqueous systems, lubricity, and flow and leveling in a variety of coatings, textile, plastic, and personal care applications. The data in the table is based on four samples.
4. Doss 70D at 0.7% add on based on the dry weight of the wrap: Doss 70D is a dialkyl sulfosuccinate anionic surfactant available from Manufacturers Chemicals LLC. The data in the table is based on four samples.
5. Cirrasol® PP862 at 1.0% add on based on the dry weight of the wrap: Cirrasol® PP862 is a non-ionic surfactant that is a blend of hydrogenated ethoxylated castor oil and sorbitan monooleate and is available from Croda International PLC of East Yorkshire, England. The data in the table is based on five samples.
6. Pluronic® P123 at 0.3 add on based on the dry weight of the wrap: Pluronic® P-123 is the tradename for a triblock copolymer manufactured by the BASF Corporation. The nominal chemical formula is $HO(CH_2CH_2O)_{20}(CH_2CH(CH_3)O)_{70}(CH_2CH_2O)_{20}H$, which corresponds to a molecular weight of around 5800 Da. Triblock copolymers based on poly(ethylene glycol)-poly(propylene glycol)-poly(ethylene glycol) are known generically as poloxamer, and similar materials are manufactured by other companies. The data in the table is based on five samples.
7. Pluronic® P123 at 0.6% add on based on the dry weight of the wrap: The data in the table is based on five samples.
8. Pluronic® P123 at 1.8% add on based on the dry weight of the wrap: The data in the table is based on five samples.
9. Pluraflo® L1060 at 0.5% add on based on the dry weight of the wrap: Pluraflo® L1060 is a non-ionic dispersant (i.e., surfactant) of an ethylene oxide propylene oxide block co-polymer and is available from the BASF Corporation of Florham Park, N.Y. The data in the table is based on four samples.
10. No treatment: No surfactant treatment is added to the base fabric prior to electret treatment and sterilization. The data in the table is based on five samples.
11. Pluronic® P123 at 0.22% add on based on the dry weight of the wrap
12. Pluronic® P123 at 0.10% add on based on the dry weight of the wrap
13. Pluronic® P123 at 0.16% add on based on the dry weight of the wrap
14. Pluraflo® L1060 at 0.20% add on based on the dry weight of the wrap

| Sample number, from above | Electret conditions | Pre-elec. TSI | Post-elec. TSI | Pre-sterilization BFE | Post-sterilization BFE | Wet Packs, out of 14 samples |
|---|---|---|---|---|---|---|
| 1 | D | 20.1 ± 0.9 | 20.4 ± 0.7 | | | 12 |
| 2 | C | 17.0 ± 0.2 | 16.4 ± 0.4 | 90 | | 3 |
| 3 | E | 20.4 ± 1.0 | 35.0 ± 21.1 | | | |
| 4 | E | 20.9 ± 0.4 | 21.7 ± 0.7 | | | |
| 5 | A | 18.8 ± 0.9 | 73.2 ± 1.1 | | | |
| 6 | F | 21.9 ± 0.7 | 59.2 ± 0.8 | 99.1 | 98.4 | 0 |
| 7 | F | 21.7 ± 0.6 | 59.1 ± 1.3 | 99.9 | 98.6 | 1 |
| 8 | F | 35.9 ± 12.2 | 54.0 ± 1.5 | | | 8 |
| 9 | A | 36.9 ± 8.5 | 60.9 ± 3.5 | | | |
| 10 | A | 41.2 ± 1.5 | 68.1 ± 1.4 | 99.9 | 99.7 | 13 |
| 11 | G | | | 98.5 | 99 | |
| 12 | G | | | 98.5 | 99 | |
| 13 | G | | | 98.5 | 99 | |
| 14 | G | | | 98.5 | 98.1 | |

Electret conditions:
A- 13.75 kV, 1.0 mA
B- 15 kV, 1.5 mA
C- Average of 13 kV, 1 mA and 12.5 kV, 0.7 mA
D- 12 kV, 0.7 mA
E- 12 kV, 1.0 mA
F- 13.75 kV, 11.25 mA
G- 15 kV, 5 mA; 5 kV, 5 mA As can be seen from the results, the first four samples, containing elements other than simply carbon, hydrogen, and oxygen, had a very small increase in TSI after electret treatment. This indicates that the BFE results would likely also be poor, as shown by sample 2, and for this reason, the more expensive BFE test was not run on the other samples with poor TSI results. Beginning with sample 5, however, the difference between the pre- and post- electret TSI was significant. The BFE data that was collected also showed good results, pre- and post- sterilization. The wet pack results were good, except for sample 8, which had a very high add on amount of the Pluronic® P123 treatment.

Electret treatment is used, as discussed above, to increase the BFE of a fabric. This treatment also increases the TSI. It is not believed that differing electret treatment conditions had a great effect on these result and is reported merely for thoroughness. The data shows that the treatments containing other than carbon, hydrogen, and oxygen (C—H—O) atoms do not show an appreciable increase in TSI after electret treatment, indicating that they do not allow the fabric to hold a charge and are therefore unsuitable for electret charging. Samples 1, 2, and 4 have little or no positive change in TSI after electret treatment. Note that sample 3 does show an average increase in TSI, but the range of results is extremely wide, leading to questions about repeatability and the value of such results. The successful candidates display large increases in TSI after electret treatment, showing that they allow the web to absorb the charge needed to increase the barrier to microbial infiltration.

Regardless of the mechanism of operation, it is clear that the treatments for Samples 5-9 that are surfactants containing only carbon, hydrogen, and oxygen (C—H—O) atoms are superior to other treatments containing silicon, phosphorus, sulfur, and the like, though amounts above 1.5% add on appear to be less promising. Treatments that are C—H—O surfactants that are essentially free of silicon, potassium, phosphorus, and sulfur provide superior TSI NaCI filtration and reduced wet packs compared to the other treatments for Samples 1-4, except at very high treatment amounts. The preferred amount of surfactant add on is between a positive amount and 1 weight percent or at most 1.5%. Treatments limited to having only C—H—O surfactants also produce fewer wet packs when compared to the same base fabric (i.e., an identical base fabric) without any treatment (i.e., sample 10).

Further, Samples 1-10 demonstrate the ability of the sterilization wrap of the present disclosure to reduce the occurrence of wet packs post steam sterilization by applying a surfactant treatment to both the outwardly-facing surface and inner-facing surface of the sterilization wrap using a dip and squeeze method, allowing the surfactant treatment to dry on the sterilization wrap, and then applying an electret treatment. Meanwhile, Samples 11-14 demonstrate that the sterilization wrap of the present disclosure can also be formed by applying an electret treatment to the sterilization wrap, then applying a surfactant treatment to the sterilization wrap using foam treatment application process, where the surfactant treatment is applied to an outwardly facing surface of the outer layer of the sterilization wrap (i.e., the layer that is not facing the items to be sterilized when wrapped in the sterilization wrap, or, in other words, the surface that is exposed to the outside environment) and then allowing the surfactant treatment to dry on the sterilization wrap.

A further embodiment of the present disclosure encompasses the application of the above-described surfactant treatment to a sterilization wrap that includes: a first panel having a permeable material having barrier properties and having a first surface and a second opposing surface, the first panel being substantially opaque or having a first level of translucence; and a second panel including a permeable material having barrier properties and having a first surface and a second opposing surface, the second panel having a level of translucence that is higher than the translucence of the first panel, the panels being joined together over at least a portion of their surfaces. The second panel may include a plurality of bond points. These bond points define discrete locations having higher translucence than locations on the permeable material of the second panel that are not bond points. For example, the plurality of bond points on the second panel may provide the second panel with at least 15 percent higher translucence than locations on the permeable material of the second panel that are not bond points. As another example, the plurality of bond points on the second panel may provide the second panel with at least 30 percent higher translucence. As yet another example, plurality of bond points on the second panel may provide the second panel with at least 45 percent higher translucence. In one aspect of the present disclosure, the permeable material of the second panel may be a permeable material that has a higher level of translucence than the permeable material of the first panel. For example, the difference in translucence between first panel and the second panel may be at least 15 percent. As another example, the difference in translucence between first panel and the second panel may be at least 30 percent. As yet another example, the difference in translucence between first panel and the second panel may be at least 45 percent. Such a sterilization wrap and related methods of use are disclosed by U.S. Patent Application Publication No. 2013/0111852 by Farmer, et al. for "Method of Using a Sterilization Wrap System" published May 9, 2013, incorporated herein by reference. Utilizing the surfactant treatment described herein with the sterilization wrap disclosed by U.S. Patent Application Publication No. 2013/0111852 to provide sterilization wrap that results in the production of fewer wet packs after steam sterilization while also allowing for significantly improved inspection of the sterilization wrap for breaches in the panel opposite the viewer by looking for light passing through the panel facing the viewer.

Another embodiment of the present disclosure encompasses the application of the above-described surfactant treatment to a sterilization wrap that has a first side colored at least a first color and an opposing side colored at least a second color that is different from the first color as generally described by U.S. Pat. No. 8,783,003 for "Method Pertaining to a Multi-Colored Sterilization Wrap", issued Jul. 22, 2014 to Czajka, Jr., et al.

As used herein and in the claims, the term "comprising" is inclusive or open-ended and does not exclude additional unrecited elements, compositional components, or procedure steps.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications, and other changes may be made to the disclosure without departing from the spirit and scope of the present disclosure. It is therefore intended that the claims cover all such modifications, alterations, and other changes encompassed by the appended claims.

What is claimed is:

1. A sterilization wrap comprising a polyolefinic nonwoven fabric having an outwardly-facing surface and an inner-facing surface, and a dried residue of an aqueously applied surfactant treatment only on the outwardly-facing surface, wherein the polyolefinic nonwoven fabric is electret treated before application of the aqueously applied surfactant treatment, wherein said surfactant treatment includes a surfactant, wherein said surfactant is essentially free of silicon, potassium, phosphorus, and sulfur, wherein the dried residue of the aqueously applied surfactant treatment is present in an amount ranging from greater than 0 weight percent to 2 weight percent based on the dry weight of the polyolefinic nonwoven fabric, wherein the surfactant treatment results in the production of fewer wet packs after steam sterilization when the packs are wrapped with said electret and surfactant treated polyolefinic nonwoven fabric sterilization wrap as compared to when the packs are wrapped with an identical electret treated polyolefinic nonwoven fabric sterilization wrap without said surfactant treatment.

2. The sterilization wrap of claim 1, wherein said electret treated polyolefinic nonwoven fabric treated with said surfactant treatment exhibits a bacterial filtration efficiency of at least 94 percent as determined according to ASTM F2101.

3. The sterilization wrap of claim 1, wherein said electret treated polyolefinic nonwoven fabric treated with said surfactant treatment exhibits a bacterial filtration efficiency of at least 97 percent as determined according to ASTM F2101.

4. The sterilization wrap of claim 1, wherein said electret treated polyolefinic nonwoven fabric treated with said surfactant treatment exhibits a bacterial filtration efficiency after electret treatment and after steam sterilization of at least 97 percent as determined according to ASTM F2101.

5. The sterilization wrap of claim 1, wherein said surfactant consists essentially of carbon, hydrogen, and oxygen atoms.

6. The sterilization wrap of claim 1, wherein said electret treated polyolefinic nonwoven fabric has a bacterial filtration efficiency after electret treatment and after steam sterilization ranging from 97 percent to 99.7 percent as determined according to ASTM F2101.

7. The sterilization wrap of claim 1, wherein said surfactant treatment is applied to said polyolefinic nonwoven fabric in an amount ranging from about 0.1 weight percent to about 1.5 weight percent based on the dry weight of said polyolefinic nonwoven fabric.

8. The sterilization wrap of claim 1, wherein the wrap comprises: a first panel comprising a permeable material having barrier properties and having a first surface and a second opposing surface, the first panel being substantially opaque or having a first level of translucence; and a second panel comprising a permeable material having barrier properties and having a first surface and a second opposing surface, the second panel having a level of translucence that is higher than the translucence of the first panel, wherein the panels are joined together over at least a portion of their surfaces.

9. The sterilization wrap of claim 1, wherein the sterilization wrap has a first side colored at least a first color and an opposing side colored at least a second color that is different from the first color.

10. The sterilization wrap of claim 7, wherein said surfactant treatment is applied to said polyolefinic nonwoven fabric in an amount ranging from about 0.2 weight percent to about 0.5 weight percent based on the dry weight of said polyolefinic nonwoven fabric.

11. A method of reducing the occurrence of wet packs post sterilization, the method comprising the steps of:
 a. providing a nonwoven fabric sterilization wrap having an outwardly-facing surface and an inner-facing surface,
 b. applying a surfactant treatment to the outwardly-facing surface, the surfactant treatment including a surfactant, wherein said surfactant consists essentially of carbon, hydrogen and oxygen atoms, to said nonwoven fabric, in an amount ranging from greater than 0 weight percent to 2 weight percent based on the dry weight of the nonwoven fabric sterilization wrap,
 c. drying said surfactant treated nonwoven fabric sterilization wrap,
 d. applying an electret treatment to said nonwoven fabric sterilization wrap before the step of applying the surfactant treatment,
 e. wrapping items to be sterilized in said surfactant treated nonwoven fabric sterilization wrap, and,
 f. steam sterilizing the wrapped items,
 wherein sterilizing the wrapped items with said electret and surfactant treated nonwoven fabric sterilization wrap results in the production of fewer wet packs after steam sterilization as compared to when the items are wrapped with an identical electret treated nonwoven fabric sterilization wrap without said surfactant treatment.

12. The method of claim 11, wherein said electret and surfactant treated nonwoven fabric sterilization wrap has a bacterial filtration efficiency of at least 94 percent as determined according to ASTM F2101.

13. The method of claim 11, wherein said electret and surfactant treated nonwoven fabric sterilization wrap has a bacterial filtration efficiency after electret treatment and after steam sterilization of at least 97 percent as determined according to ASTM F2101.

14. The method of claim 11, wherein said surfactant is essentially free of silicon, potassium, phosphorus, and sulfur and/or said surfactant treatment is applied to said nonwoven fabric sterilization wrap in an amount ranging from about 0.1 weight percent to about 1.5 weight percent based on the dry weight of said nonwoven fabric sterilization wrap.

15. The method of claim 11, wherein said nonwoven fabric sterilization wrap comprises: a first panel comprising a permeable material having barrier properties and having a first surface and a second opposing surface, the first panel being substantially opaque or having a first level of translucence; and a second panel comprising a permeable material having barrier properties and having a first surface and a second opposing surface, the second panel having a level of translucence that is higher than the translucence of the first panel, wherein the panels are joined together over at least a portion of their surfaces.

16. The method of claim 11, wherein said nonwoven fabric sterilization wrap has a first side colored at least a first color and an opposing side colored at least a second color that is different from the first color.

17. The method of claim 11, wherein said electret and surfactant treated nonwoven fabric sterilization wrap has a bacterial filtration efficiency after electret treatment and after steam sterilization ranging from 97 percent to 99.7 percent as determined according to ASTM F2101.

18. The method of claim 11, wherein said surfactant is essentially free of silicon, potassium, phosphorus, and sulfur and/or said surfactant treatment is applied to said nonwoven fabric sterilization wrap in an amount ranging from about 0.2 weight percent to about 0.5 weight percent, based on the dry weight of said nonwoven fabric sterilization wrap.

* * * * *